United States Patent
Van Hulten et al.

(10) Patent No.: US 11,185,489 B2
(45) Date of Patent: Nov. 30, 2021

(54) ORAL CARE PARTICLES AND SYSTEM FOR THE ADMINISTRATION THEREOF

(71) Applicant: KONINKLIJKE PHILIPS N.V., Eindhoven (NL)

(72) Inventors: Maaike Cornelia Johanna Wilhelmina Van Hulten, Waalre (NL); Bart Gottenbos, Budel (NL); Carl Glasse, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/496,462

(22) PCT Filed: Mar. 23, 2018

(86) PCT No.: PCT/EP2018/057413
§ 371 (c)(1),
(2) Date: Sep. 23, 2019

(87) PCT Pub. No.: WO2018/177915
PCT Pub. Date: Oct. 4, 2018

(65) Prior Publication Data
US 2020/0368138 A1    Nov. 26, 2020

(30) Foreign Application Priority Data

Mar. 29, 2017  (EP) ..................... 17163594

(51) Int. Cl.
*A61Q 11/00* (2006.01)
*A61K 6/17* (2020.01)
(Continued)

(52) U.S. Cl.
CPC .................. *A61K 8/86* (2013.01); *A61K 6/17* (2020.01); *A61K 8/731* (2013.01); *A61K 8/8129* (2013.01);
(Continued)

(58) Field of Classification Search
None
See application file for complete search history.

(56) References Cited

U.S. PATENT DOCUMENTS

| | | |
|---|---|---|
| 5,869,029 A | 2/1999 | Graff-Andersen et al. |
| 2003/0044442 A1 | 3/2003 | Stanier |

(Continued)

FOREIGN PATENT DOCUMENTS

| | | |
|---|---|---|
| EP | 0346708 A2 | 12/1989 |
| JP | 2001163768 A | 6/2001 |

(Continued)

OTHER PUBLICATIONS

Hossein Omidian. "Improved Superabsorbent Polymers." PhD Thesis, Brunel University, Sep. 1997, pp. 1-180 and 3 initial pages (183 total sheets). (Year: 1997).*

(Continued)

*Primary Examiner* — Isaac Shomer

(57) ABSTRACT

Disclosed is a system and method for the delivery, into interdental spaces, of oral care active agents contained in particles. The particles are made of one or more superabsorbent polymers (SAP), and are of size generally small enough to be easily applied into an interdental space. To this end, the particles typically have a length of below 1.5 mm. By virtue of the SAP's ability of absorbing several times its own weight in water, the particles will swell once in contact with saliva. As a result, the volume of the particles as applied in between teeth increases by at least eight times, thereby effectively making the particles larger than the average interdental gap size. The particles, once swollen, are thus held more firmly between the walls of the interdental space, thus preventing them from being easily washed away.

13 Claims, 2 Drawing Sheets

(51) Int. Cl.
 *A61K 8/86* (2006.01)
 *A61K 8/73* (2006.01)
 *A61K 8/81* (2006.01)

(52) U.S. Cl.
 CPC .......... *A61K 8/8147* (2013.01); *A61K 8/8158* (2013.01); *A61Q 11/00* (2013.01); *A61K 2800/594* (2013.01); *A61K 2800/60* (2013.01); *A61K 2800/87* (2013.01); *A61K 2800/92* (2013.01)

(56) References Cited

U.S. PATENT DOCUMENTS

| | | | |
|---|---|---|---|
| 2003/0215401 A1* | 11/2003 | Estrada | A61K 8/19 424/49 |
| 2005/0080182 A1* | 4/2005 | Ahmed | C08J 3/03 524/458 |
| 2006/0188452 A1* | 8/2006 | Rochat | A61K 8/19 424/49 |
| 2007/0202063 A1 | 8/2007 | Dihora | |
| 2007/0237741 A1* | 10/2007 | Figuly | A61K 31/785 424/78.18 |
| 2013/0028978 A1* | 1/2013 | Mao | A61K 35/28 424/497 |
| 2013/0340185 A1* | 12/2013 | Patel | A61C 15/00 15/104.93 |
| 2014/0308625 A1 | 10/2014 | Fairley et al. | |

FOREIGN PATENT DOCUMENTS

| | | | | |
|---|---|---|---|---|
| JP | 2007091686 A | | 4/2007 | |
| KR | 100965439 B1 | | 6/2010 | |
| WO | 2007062414 A1 | | 5/2007 | |
| WO | 2011094613 A1 | | 8/2011 | |
| WO | 2016046141 A1 | | 3/2016 | |
| WO | 2016050573 A1 | | 4/2016 | |
| WO | WO-2016050573 A1 | * | 4/2016 | .......... A61C 15/047 |
| WO | 2016097927 A1 | | 6/2016 | |
| WO | 2016157140 A1 | | 10/2016 | |
| WO | 2017207533 A1 | | 12/2017 | |

OTHER PUBLICATIONS

PCT/2018/057413, ISR & WO, dated Jun. 11, 2018, 19 Page Document.

* cited by examiner

ORAL CARE PARTICLES AND SYSTEM FOR THE ADMINISTRATION THEREOF

CROSS-REFERENCE TO PRIOR APPLICATIONS

This application is the U.S. National Phase application under 35 U.S.C. § 371 of International Application No. PCT/EP2018/057413, filed on Mar. 23, 2018, which claims the benefit of European Patent Application No. 17163594.9, filed on Mar. 29, 2017. These applications are hereby incorporated by reference herein.

FIELD OF THE INVENTION

The invention is in the field of oral care, and pertains to the use of polymer particles for the administration of oral care agents to an oral cavity of a subject. The invention also relates to a system and a method for such administration as well as to a kit of parts and preparation to be used with such administration.

BACKGROUND OF THE INVENTION

In order to maintain or restore oral health many oral care agents exist that are generally non-invasively administered to the oral cavity which includes e.g. teeth and gums. Examples of such agents are fluoride, remineralization agents, antiplaque agents, anti-tartar agents, anti-gingivitis agents, anti-bacterial agents, and others.

Such agents can be administered from toothpastes and/or oral rinse liquids. However, due to the typical environment of the oral cavity, e.g. having saliva present, a standard difficulty in the art is that such agents are quickly reduced in concentration after their administration. Therefore they cannot protect the oral cavity for long, and regular re-administration, sometimes several times per day, is often needed for good results.

In recent years administration of oral care agents via particles such as for example solid particles, gel particles, or vesicles has become popular. Such particles may serve as carriers of the oral care agents capable of providing a controlled release, e.g., a sustained release, of the oral care agents when delivered to an oral cavity. Particles, such as for example gel particles, may have a low volume of solids (typically 1-2%) and therefore have a large volume available for carrying oral care agents. The sustained release of oral care agent could counteract the natural concentration loss of agents due to oral cavity conditions as described herein above unless the particles suffer the same fate of quick concentration reduction as the oral care agents do.

It is noted that substantivity, such as retention in the interproximal spaces, plays a particular role in view of the non-invasive character of the administration of oral care agents. This is different from injecting a drug into the body, in order to have it taken up in circulation and act systemically rather than locally.

It is an ongoing challenge to apply the particles to the oral cavity such that they are less prone to removal from the oral cavity by natural processes such as e.g. spitting or swallowing. Thus, it is desired to provide the oral care agents with a better substantivity, i.e., a longer residence time in the oral cavity, than would be naturally given. One way of achieving this is by depositing and retaining the particles in the interproximal spaces. This then combines with the fact that the interproximal space is the area in the oral cavity that is most prone to oral disease, since plaque and/or bacteria causing disease such as for example gingivitis and caries can easily accumulate in these spaces. Delivery of sustained release oral care agents in the interproximal area may thus reduce or prevent such diseases more effectively.

Oral care particles, also for controlled release (such as sustained release) would conventionally be delivered from suspensions simply applied by 30 seconds rinsing with 20 to 30 milliliters of a particle containing formulation. This is for example done with common antimicrobial mouth rinses. However for delivery in the interproximal space this is far from optimal. Particularly, most of the formulation will be spit out and most of the particles will not adhere to the narrow interproximal areas. The interproximal areas might not even be treated at all. Application of excessive amounts of slow release particles may slightly improve this situation, but the improvements remain marginal while the use of such excessive amounts is economically undesirable.

JP 2001163768A describes another alternative for sustained release of oral care agents using a preparation that has a shape that essentially allows it to be inserted into an interdental space. Typically, this is described as a stick-shape, but other shapes (column, cone, plate, columnar, prism, cone, or wedge) are foreseen. The application of the preparation to such interdental areas will generally need to be done manually. Considering the relatively small size of the sticks, this is quite an elaborate task.

SUMMARY OF THE INVENTION

There is thus a need for improved ways of providing sustained release of oral care agents from interdental spaces within the oral cavity.

The aforementioned need is at least partially fulfilled by the invention as defined by the independent claims. The dependent claims provide advantageous embodiments.

In a first aspect the invention concerns the use of one or more polymer particles for the delivery of an oral care agent to an oral cavity of a subject, wherein the one or more polymer particles each:

have an initial volume and at least one size dimension equal to or smaller than 1.5 millimeter, and comprise a water-absorbent polymer for absorbing water in an amount that causes the volume of each one of the one or more polymer particles to increase to at least eight times the initial volume.

In a second aspect the invention concerns a system for the application of an oral care agent to an oral cavity of a subject, the system comprising:

(a) a first container holding one or more polymer particles each having an initial volume and at least one size dimension equal to or smaller than 1.5 millimeter; wherein the particles comprise a water-absorbent polymer for absorbing water in an amount that causes the volume of each of the one or more polymer particles to increase to at least eight times the initial volume;

(b) a second container holding the oral care agent;

(c) an applicator for the interdental delivery of the polymer particles comprising the oral care agent;

In a third aspect the invention concerns a kit of parts for the application of an oral care agent to an oral cavity of a subject, the kit of parts including:

a first part comprising one or more polymer particles each having an initial volume and at least one size dimension equal to, or smaller than 1.5 millimeter; wherein the particles comprise a water-absorbent polymer for absorbing water in an amount that causes the volume of each of the one or more polymer particles to increase to at least eight times the initial volume; and a second part comprising the oral care agent.

In a fourth aspect the invention concerns a preparation comprising one or more polymer particles for the delivery of an oral care agent to an oral cavity of a subject, the one or more polymer particles having an initial volume and at least one size dimension equal to or smaller than 1.5 millimeter; wherein the one or more polymer particles comprise:

a water-absorbent polymer for absorbing water in an amount that causes the volume of each one of the one or more polymer particles to increase to at least eight times the initial volume, particularly a super absorbent polymer selected from the group consisting of sodium polyacrylate, crosslinked polymers based on sodium polyacrylate; polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile; and the oral care agent.

In yet another aspect the invention concerns a method for administering an oral care agent to the oral cavity of a subject, the method comprising:

providing one or more polymer particles each having an initial volume and at least one size dimension equal to or smaller than 1.5 millimeter, and each comprising:

a water-absorbent polymer for absorbing water in an amount that causes the volume of each one of the one or more polymer particles to increase to at least eight times the initial volume; and the oral care agent; and delivering the one or more polymer particles to the oral cavity.

The invention is based on the judicious insight to introduce oral care agents into interdental spaces by including such agents in particles that are small enough to fit into said spaces, and that will thereupon undergo swelling caused by their uptake of water to an extent allowing the particles to remain fixed in said interdental spaces. To this end the particles have at least one size dimension that is smaller than an average distance of approximately 1.5 millimeters between neighboring teeth (i.e. the distance spanning an interdental space.

Such particles, because of their small size before application can be advantageously applied to the oral cavity and in particular the interdental spaces. This may be advantageously done using a jetting device, typically releasing air or water under pressure.

It is further noted that while JP 2001163768A discloses sustained release preparation for oral care agents, these are not preparations according to the invention as they are preferably intended to show little moisture swelling. JP 2001163768A particularly addresses a problem that some of the polymer materials used, result in moisture-swelling in the mouth.

BRIEF DESCRIPTION OF THE DRAWINGS

The invention will be described with reference to the following Figures in which the drawings are schematic.

DETAILED DESCRIPTION OF EMBODIMENTS

Figure 1:
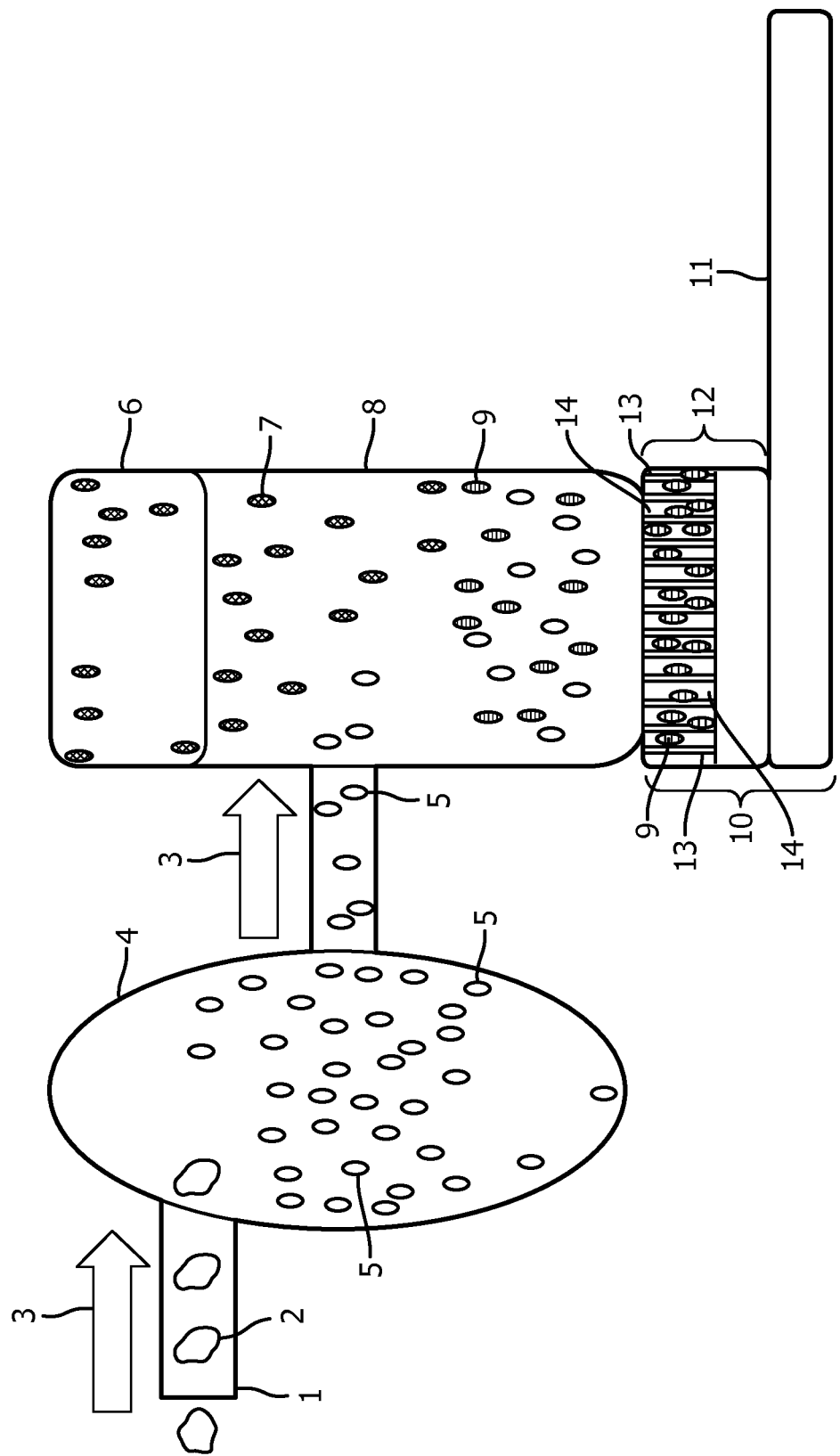
FIG. 1 is a first system for the delivery of particles in accordance with the invention.

The description of features and characteristics of among others the particles, the polymers, and the oral care agents with their advantages are applicable to all aspects of the invention, being e.g. the use, methods system, preparation, and kit of parts. They can be used in combination unless other specified otherwise.

The terms "interdental" and "interdental space" refer to the space, or gap, between teeth. In the art this is generally also referred to as "interproximal" and "interproximal space."

The invention relates to polymer particles (and their use) that are prepared prior to the oral (interdental) delivery thereof, i.e., the polymer particles comprise the oral care agent at least when it is actually applied to the oral cavity. While this does still include the option of having separately the polymer particles and the oral care agent and adding the oral care agent to the polymer particles before delivering the ensemble to the oral cavity, this is different from compositions, which may be particulate, and that are formed in situ in the mouth. The invention thereby presents a new use of polymer particles that are capable of substantive swelling in moisture such that the swelling causes entrapment of the particles. The invention also provides a system that comprises at least one container for holding the particles and an oral care agent. Both the use (i.e., a method of using pre-formed polymer particles) and the system (comprising a container already holding pre-formed particles) reflect that the particles in the present invention are not made in situ during their delivery.

The particles of the preparation have an initial volume and size constraint such that they fit in an interdental space. It will thus be understood that, before swelling, which occurs under the influence of moisture present in the mouth, the particles are thus smaller than the gap size of the interdental spaces into which they are to be introduced. By way of general guidance, it is noted that typical gaps of interdental spaces are around 1 millimeter (mm) to around 1.5 millimeter at their widest point. Accordingly, at least one size dimension of the polymer particles, such as e.g. the length, width, height or diameter of the polymer particles generally is equal to or smaller than the 1.5 millimeter, and preferably equal to or smaller than 1 millimeter.

The polymer particles can have different shapes, e.g. spherical, prolate (elongate) spherical, oblate spherical, or irregular variations of such shapes. Accordingly, the particles can have different (size) dimensions in different directions. It is therefore clarified that the particle size can be defined with reference to three orthogonally directed dimensions (commonly understood as an x-axis, y-axis, and z-axis), corresponding to e.g the earlier mentioned length, width and height respectively. However, the size direction can also be a body diagonal or diameter of a polymer particle. It is preferred that the at least one size dimension equal to or smaller than 1.5 millimeter is the largest dimension of the polymer particle. This means that in every direction the size of the particle is smaller than the interdental gap. Hence, orientation of the particle with regard to the gap is of less influence on whether the particle is actually able to enter the gap.

With reference to the aforementioned particle sizes, of these three size dimensions there is at least one that is equal to or smaller than 1.5 mm, preferably at most 1 mm, and the shortest dimension is at least 0.001 mm, preferably at least 0.1 mm. With reference to the typical interdental space gap size, it is preferred that at least the largest dimension is in a range between 0.2 mm and 1.2 mm, such as between 0.3 mm and 1 mm, such as between 0.4 mm and 0.8 mm. Preferably, in all of the above three dimensions, the lengths are within a range between 0.5 mm and 1 mm.

In a preferred embodiment, the particles have a rounded or preferably substantially spherical shape. Thereby the spheres have a diameter that preferably is in the range of from 0.1 mm to 1.5 mm, such as from 0.2 mm to 1.2 mm, such as from 0.3 mm to 1 mm, such as from 0.4 mm to 0.8 mm. Preferably, the diameter of such particles is within a range of from 0.5 mm to 1 mm.

In another embodiment, the particles have an elongated shape. An advantage hereof is that such particles are capable of filling a larger part of the interdental space. Thereby the longest dimension preferably is 1.5 to 3 times as long as the shortest dimension. A preferred elongated shape is a prolate spherical shape. This shape can have rounded ends or pointed ends.

It will be understood that for all particles, as a result of swelling due to uptake of water, their initial shape may change, also depending on the available freedom of expansion as available within a particular interdental space. E.g., where swelling generally will occur with the same order of magnitude in all directions, a particle that is free to expand in all directions, will generally retain a swollen shape corresponding to the original shape before swelling. For a particle that has been placed in a confinement, such as present in between teeth, the swelling may become inhibited in those directions where a counter force is experienced as provided by interdental surfaces of teeth and/or gums. It is this effect that causes that the swollen particle will become fixed against such surfaces.

In order for these particles to be deliverable as intended, the particles are, prior to delivery, in discrete form. This does not exclude some agglomeration of particles to occur, but it will generally be possible to identify, and separately apply, a single particle of the invention.

The polymer particles used in the invention will suitably comprise an orally acceptable release matrix. This refers e.g. to materials that are edible or inert, so as to allow accidental swallowing by a human subject.

The invention makes use of polymer particles capable of swelling (increasing their size or volume) due to uptake of water when brought in contact with moisture in any form such as vapor, mist, liquid. In particular they have this ability when they are brought in contact with saliva as moisture is particularly present in the oral cavity (also referred to as mouth) of a subject (human or animal) as part of saliva.

In accordance with the invention, the water-absorption is such as to allow the particles to swell in the presence of moisture to at least eight times their initial volume. The initial volume is the volume of the particles before delivery to the oral cavity. It may be a dry volume, if no pre-swelling has taken place, but it may also be a volume after pre-swelling to a defined value as will be explained herein below.

The swelling (volume increase) generally corresponds to an expansion, in three spatial dimensions (such as length, width, and height), to at least two time the original size (which implies $2^3$ in volume). It will be understood that the spatial expansion of size in theory can be even in all dimensions, but may also be irregular, i.e. not having the same extent in all directions. The increase of the initial volume is at least to a volume that is equal to or larger than eight times the initial volume.

Preferably, the volume increase exceeds the aforementioned factor of eight. Typical volume increases are by 10 to 100 times, such as 20 to 80 times, such as 30 to 60 times or, e.g. 25 to 50 times.

To achieve the above mentioned volume increase, the polymer particles comprise or consist of at least one water-absorbent polymer. Thus in embodiments it may include a mixture of such polymers as will be elucidated herein below. The polymer should be capable of absorbing an amount of water exceeding its own weight, and preferably this is 50 to 500 times its own weight, such as 100 to 300 times.

As a test to measure the water uptake capacity of polymer particles, the swelling (and not dissolving) behavior can be established by immersing a polymer particle in water and allowing it to stand for a pre-determined period of time such as 5 minutes, or 10 minutes, or 20 minutes or even a preferred 60 minutes at a predetermined temperature such as 20° C., or 37° C. to mimic temp of an oral cavity of a subject and then removing the particles using tweezers. The test is preferably done at 37° C. during 60 minutes. The particles' dimensions can then be measured using standard laboratory equipment, such as a vernier (or nonius) caliper. The method is based, by analogy, on a method disclosed in a review on Superabsorbent Polymer Materials by Mohammad J. Zohuriaan-Mehr and Kourosh Kabiri, in Iranian Polymer Journal, 17 (6), 2008, 451-477. Therein the free-absorbency capacity if SAP is determined by placing a SAP sample of a weight (W0) of 0.1-0.3 g into a tea-bag (acrylic/polyester gauze with fine meshes) and dipping the bag in an excess amount of water or saline solution for one hour to reach the equilibrium swelling. Then excess solution is removed by hanging the bag until no liquid is dropped off. The tea bag is weighed (W1) and the swelling capacity Sc is calculated by equation 1 below.

$$Sc = (W1 - W0)/W0 \quad (1)$$

In addition to determining the volume swelling as above, it will be understood that the tests can also be used for determination of weight-increase by swelling of particles.

In relation to the option of using partly pre-swollen particles as will be described herein below, one can perform the test according to above protocols, but one can also additionally use a drying step before exposing the particles to the moisture to return them to their dry volume before performing the swelling capability test. This dry volume can be used to assess the extent of pre-swelling as related to the full absorption capacity of the polymer particle.

Suitable moisture-swellable polymers are well known in the art. In the present invention, such polymers used are preferably, but not necessarily, the ones that are generally indicated as "super absorbent polymer"(SAP). This refers to polymers that are able to absorb more liquid (in this case water) than their own weight, and thereby form a hydrogel. As such they form part of the group of hydrogel-forming water absorbent polymers which is useful for the invention, even if not of the SAP type. In the hydrogel forming polymers (other than with materials that dissolve upon taking up water) the absorption of water results in a generally large volume increase (i.e., swelling) during absorption. In general, the moisture-swellable polymers used in the invention are hydrophilic and they contain chemical cross-links between polymer strands so as to maintain a particle shape when exposed to water.

Examples of known SAP include: crosslinked polymers based on sodium polyacrylate; polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. A preferred SAP is sodium polyacrylate.

In order to further improve polymer particle retention at the delivery area (e.g. interdental space) beyond that provided by the swelling of the polymer particles, the polymer particles of the invention can be coated with a layer of a muco-adhesive material, such as e.g. chitosan which is an orally acceptable material.

In the invention, the particles comprise at least one oral care agent (but there may also be a mixture of mutually compatible agents) before they are delivered to the oral cavity. It is to be understood that when the polymer particles including the oral care agent have been delivered to the oral cavity, the polymer particle and the oral care agent have been chosen and combined in such a manner that they can release the oral care agent. Thus, binding or retainment of the oral care agent within the particle is such that under conditions that govern an oral cavity, the oral care agent can be released. Thus, the oral care agent can be physically retained by the polymer particles only to be released after the swelling (pore size increase, solubility in water etc.). In some instances the oral care agent can also be chemically bound the polymer particle, but either this should result in the oral care agent being able to exert its function without further release (for example as it may be at the surface of the particle) or the chemical bonding should be removed/reversed. The latter may be achieved for example by hydrolysis of a hydrolysable bond between polymer particle and agent under conditions present in the oral cavity. Esters may provide such bonding.

To have polymer particles include an oral care agent can be achieved with polymer particles that are pre-loaded with the oral care agent. This loading can be at the surface of the polymer particle via any type of physical adhesion process, at the inside or bulk of the polymer particle, or both. Thus, for example, dry polymer particles may have been exposed to the oral care agent. In one example the polymer particles are impregnated with the oral care agent. This may be achieved by exposing the dry polymer particles to a solution of known concentration of oral care agent in a solvent for some time, followed by separation of the impregnated particles form the solution and drying (removal of the solvent of the solution) of the polymer particles to leave the oral care agent loaded on or in the polymer particles. If the solvent was an aqueous solvent, then the dry particles may have been swollen during the impregnation. The drying can take place to full extent to leave the dry particles or only partially to leave partially pre-swollen particles.

In another embodiment, the oral care agent is provided separately, possibly and preferably in an aqueous fluid dispersion or solution. In that event, the particles are brought into contact with said fluid before, during or immediately after their interdental delivery. It will be understood that the oral care agent or even the entire aqueous fluid or solution are then chosen to be readily absorbed by the polymer particles. Note however, that the resulting polymer particle still has the above-identified size upon delivery or when delivered to the oral cavity and the interdental space even if partially pre-swollen (as will be described herein below) and is thus still capable of (further) swelling when in contact with saliva. Thus, immediately after their delivery, the polymer particles have not reached their maximum volume increase. In this embodiment it is preferred that the incorporation of the oral care agent in and/or on the polymer particles takes place shortly before the interdental delivery, e.g., by allowing the particles and the fluid to be combined near an exit of an applicator. Applicators will be described herein below.

In another embodiment, the particles are partially pre-swollen by having been allowed to absorb an aqueous liquid, such as water or, e.g., a physiological salt solution or an aqueous solution preferably also comprising an oral care agent. It will be understood that the partially pre-swollen particle will have a size as defined above, and will be capable of at least eight-times volume swelling, such as 10 to 50 times, such as 20-30 times, e.g. 25 times. An advantage of pre-swelling is that the particles, whilst still fully capable of working in accordance with the principle of the invention, can be more easily applied manually, with a toothbrush, or with an electrical toothbrush. The pre-swelling is generally to at most 25% of the particle's full absorption capacity, such as to at most 12.5%, such as at most 10%. Generally, the pre-swelling is to at least 5% of the full absorption capacity, such as at least 7.5%, such as at least 10%. The skilled person can determine, without undue experimentation, whether a pre-swollen particle complies with the requirements for use in the present invention. Accordingly, the pre-swollen particle can be subjected to the immersion test described above.

It will be understood that the smaller the polymer particles before swelling are, the better they may be applied in smaller spaces in the oral cavity. However, it will also be understood that with smaller initial volume of the particles in general a higher volume increases will be needed in order for such particles to be retained in an interdental space as a result of particle clamping alone or in combination with other effects. For example in the event of a spherical particle of 1 mm diameter, the volume is $^4/_3\pi r^3=0.52$ mm$^3$. Using a superabsorbent polymer having a 50 times volume swelling behavior, the size would become 25 mm$^3$, which is suitable to fill up an average interdental space. In the event of particle having a diameter below 0.4 mm, using a SAP with 50× volume increase will result in a particle having a volume of at most 1.65 mm$^3$. Calculated for a sphere, such a particle has a diameter equal to twice the cube root of $(1.65/^4/_3\pi)$, i.e., a most 1.47 mm. In that event a single particle may not be sufficiently retained by clamping alone and an interesting embodiment involves using multiple particles that form an agglomerate. In another example, starting with a 1 mm diameter and providing an at least eight times volume increase will push the particle against the walls of the interproximal space and may therewith clamp the particle between parts of different teeth abutting the interdental space.

In the tables hereinafter, several calculation examples are given for different particle sizes and different degrees of swelling. For the sake of the calculations, the particles have been assumed to be spherical. Accordingly, in one example, for a particle having a diameter of 1.4 mm, and thus a radius r of 0.7 mm, the volume $^4/_3\pi r^3=1.44$ mm$^3$. The result of, e.g., 25 times volume swelling would then be a volume of a swollen particle of 36 mm$^3$. The diameter of the swollen particle (again, for the sake of the calculation assume to be spherical) is then calculated by dividing 36 by $^4/_3\pi$, and taking twice the cube root of the outcome thereof, i.e., 4.10. In table 1 a volume swelling of fifty times is used, in table 2 twenty times, and in table 3 ten times. In each case all table entries except the smallest particle indicated, marks particles that, after the stated amount of swelling, are sufficiently large so as to be retained between interdental spaces of typical size.

TABLE 1

| Radius (r = ½D) before swelling (mm) | Volume (⁴⁄₃πr³) if spherical (mm³) | Result of 50x volume swelling (mm³) | Diameter of swollen particle (mm) |
|---|---|---|---|
| 0.5 | 0.52 | 25 | 3.63 |
| 0.4 | 0.27 | 13.5 | 2.95 |
| 0.3 | 0.11 | 5.5 | 2.19 |
| 0.2 | 0.033 | 1.65 | 1.47 |
| 0.1 | 0.004 | 0.2 | 0.73 |

TABLE 2

| Radius (r = ½D) before swelling (mm) | Volume (⁴⁄₃πr³) if spherical (mm³) | Result of 20x volume swelling (mm³) | Diameter of swollen particle (mm) |
|---|---|---|---|
| 1 | 4.19 | 83.8 | 5.43 |
| 0.75 | 1.77 | 35.4 | 4.07 |
| 0.5 | 0.52 | 10.4 | 3.63 |
| 0.4 | 0.27 | 6.75 | 2.71 |
| 0.3 | 0.11 | 2.2 | 1.61 |
| 0.2 | 0.033 | 0.66 | 1.08 |

TABLE 3

| Radius (r = ½D) before swelling (mm) | Volume (⁴⁄₃πr³) if spherical (mm³) | Result of 8x volume swelling (mm³) | Diameter of swollen particle (mm) |
|---|---|---|---|
| 1 | 4.19 | 33.5 | 4.00 |
| 0.5 | 0.52 | 4.16 | 2.00 |
| 0.25 | 0.065 | 0.52 | 1 |

The invention serves to deliver oral care agents. These may be therapeutic and/or prophylactic agents or non-therapeutic oral care agents such as agents that have a cosmetic effect.

Thus the invention may be directed to methods, uses, preparations and kits of parts for maintaining or improving oral health. In such cases the oral care agents have the prophylactic and/or therapeutic use.

The invention may be directed to methods, uses, preparations and kits of parts for cosmetic purposes. In such cases the oral care agents have cosmetic effects.

In particularly, oral care agents are agents for which it is desired to be administered into the interdental (interproximal) spaces.

Preferred agents are selected from the group consisting of antiplaque agents, anti-tartar agents, anti-gingivitis agents, anti-caries agents, anti-bacterial agents, anti-periodontitis agents, mineralization agents, bleaching agents, and combinations thereof. With reference to the advantage of being well-retained in interdental spaces, and particularly for the sustained release of such agents, the preferred agents for use in the present invention are anti-bacterial agents. These include, for example, phenolics and salicylamides, and sources of certain metal ions such as zinc, copper, silver and stannous ions, for example in salt form such as zinc, copper and stannous chloride, and silver nitrate. These are present in art-known small quantities when used. Typical oral care agents in common usage are chlorhexidine digluconate, cetylpyridinium chloride, stannous fluoride, sodium fluoride, hydrogen peroxide, zinc citrate, benzethonium chloride, zinc lactate, phenolic compounds (e.g., thymol, menthol, eucalyptol), triclosan, herbal extracts (e.g. sanguinarine).

The invention not only pertains to the methods and uses of the polymer particles, but also to the aspects of preparations or kits of parts including the particles and the oral care agent. A preparation can be a simple composition of the polymer particles and the oral care agent, but it may also encompass other components. Such components can be for changing taste or odor such as with fragrances and flavoring agents. These are also orally acceptable components.

In yet another aspect, the invention is a system comprising a container holding the aforementioned particles. This container can be an integrated compartment of an applicator device, a separate compartment that can be attached to an applicator device, or a separate tube or flask from which particles can be loaded into an applicator.

The system of the invention further comprises an applicator for the interdental delivery of the aforementioned particles with one or more oral care agents. In one embodiment, these agents are contained in the particles, i.e., the particles are pre-loaded with the agent or agents. In another embodiment, the oral care agent is provided separately in an aqueous fluid. In that event, the particles are brought into contact with said fluid before, during or immediately after their interdental delivery. It will be understood that the particles will readily absorb the fluid with the oral care agent. The resulting particle still has the above-identified size, i.e., represented by a largest dimension below 1.5 mm, and still is capable of swelling when in contact with saliva. I.e., the particles have not reached their maximum volume increase prior to being administered. In this embodiment it is preferred if the incorporation of the oral care agent takes place shortly before the interdental delivery, e.g., by allowing the particles and the fluid to be combined near an exit of an applicator.

In another embodiment, the particles are pre-swollen by having been allowed to absorb an aqueous liquid, such as water or, e.g., a physiological salt solution or an aqueous solution of an oral care agent. It will be understood that the pre-swollen particle will have a size as defined above, and will be capable of at least eight-times volume swelling, such as 10 to 50 times, such as 20-30 times, e.g. 25 times. An advantage of pre-swelling is that the particles, whilst still fully capable of working in accordance with the principle of the invention, can be more easily applied manually, with a toothbrush, or with an electrical toothbrush. The pre-swelling is generally to at most 25% of the particle's full absorption capacity, such as to at most 12.5%, such as at most 10%. Generally, the pre-swelling is to at least 5% of the full absorption capacity, such as at least 7.5%, such as at least 10%. The skilled person can determine, without undue experimentation, whether a pre-swollen particle complies with the requirements for use in the present invention. Accordingly, the pre-swollen particle can be subjected to the immersion test described above.

The applicator can generally be any device suitable to push, press, blow, or otherwise apply one or more particles onto the relatively small surface available in between teeth. In the event of dry particles, pre-loaded with an oral care agent, an interesting application method is by means of an oral irrigator. Thereby the particles are combined with a source of liquid, and jetted into the interdental spaces. This can be carried out particularly in the manner described in WO 2016/05073, the disclosure of which is incorporated by reference herein. In the event of using particles that are not pre-swollen, and notably if the particles are relatively small and intended for a relatively large absorption, it is preferred to apply the particles using a jetting device, such as an oral irrigator, particularly having one or more nozzles facilitating the interdental application of small particles. Such an application device can also be a dental tray having one or more nozzles pointed at interdental spaces.

Delivery of the swelling particle between the teeth preferably comprises the application with some force to be able to push the particle out of a device and place it in the interdental space. This can, e.g., be done by a brush, preferably using a brush head designed for such particle delivery. To make the application of the particles easy and efficient a device can be used as shown in FIG. 1, said figure reflecting a system for the interdental delivery of oral care agents in accordance with the invention.

Thereby first dry polymeric beads are applied on a brush and then an active agent solution, after which the particles can be delivered (not fully swollen yet, as the liquid volume can be limited at this stage). In the figure, the following elements are schematically indicated:

1. Air inlet into the system;
2. Air;
3. Arrow indicating the direction of air flow;
4. Reservoir for SAP particles;
5. SAP particles;
6. Reservoir for a liquid oral care agent, such as an aqueous solution;
7. Liquid oral care agent;
8. Mixing (or precipitation) chamber;
9. SAP particles mixed with liquid oral care agent;
10. Manual application device in the form of a brush having short and wide bristles adapted to hold SAP particles loaded with oral care agent;
11. Handle;
12. Brushhead;
13. Bristles;
14. Space between bristles.

Alternatively a space by space delivery device is used. Thereby an application device can be configured so as to allow dry SAP, or at least still swellable, SAP particles to absorb a desired amount of liquid active agent (such as an aqueous solution or suspension comprising an oral care active agent) just prior, during and/or immediately after delivery in the interdental space. Dry particles can be put in a cartridge which can be placed in the delivery device. The delivery device can then add some liquid to the cartridge such that a hydrogel is formed (partially swollen), or the liquid is jetted or dripped on the particle by the device after interdental delivery. Single particles can be applied with the delivery device to each interdental space, where they can further swell and get stuck between the teeth.

Figure 2:
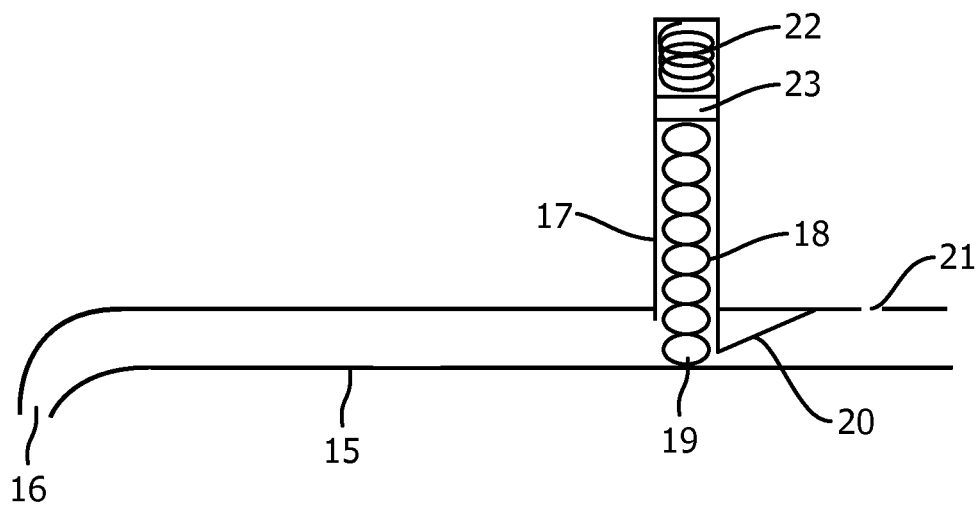
FIG. 2 is a second system for the delivery of particles in accordance with the invention.

The foregoing embodiment is schematically illustrated in FIG. 2. This shows nozzle, e.g. a nozzle fitting on an air-assisted oral irrigator such as AirFloss®. The nozzle is provided with a cartridge for dry particles, allowing these particles to be delivered to the interproximal space using an air pulse the AirFloss air pulse. Each air flow pulse serves to transport the next particle from the cartridge to the interdental space. The next particle, prior to delivery, is typically held in a position ready to be delivered (typically, for a vertically placed cartridge, this will be the lowest particle). The force for delivery can be conventionally provided by a spring pushing against a row or pile of particles, either directly or indirectly via a plunger or a disk. The air pressure is limited by using a constriction in front of the particles and an air leak hole at the nozzle base, in order not to shoot the particle through the interdental space, rather than applying it there. After the pulse a new particle is loaded in the nozzle from the particle cartridge, in this case using pushing force from a spring. The following elements are shown in the figure:

15. Nozzle;
16. Nozzle exit;
17. Cartridge;
18. SAP particles with oral care agent;
19. Next particle to be delivered;
20. Constriction to limit air pressure;
21. Air-leak hole;
22. Spring;
23. Disk.

The invention also pertains to a system for the administration of particles as defined hereinabove, to the interproximal spaces of a subject's teeth. The system of the invention comprises a container holding polymer particles and one or more oral care agents, as substantially described above. The particles can be loaded with the oral care agents, and/or the oral care agents can be provided separately and be combined with the particles before delivery. In the system of the invention, separately provided oral care agents can be held in a container that is part of an applicator device, or they can be provided from a separate source, such as a tube or a flask.

The preparation or kit of parts of the invention preferably includes the containers of the system of the invention such that the kit of parts is a replenishment of the system. The containers may be disposable when empty.

The system of the invention further comprises an applicator for the interdental delivery of said particles with said one or more oral care agents; the applicator device is configured so as to be loaded with particles in a non-swollen or pre-swollen state, and to allow applying said particles into interproximal spaces. This can, e.g., be done by means of a pressure device, such as a fluid jet generator, more preferably an oral irrigator.

Jet generating devices such as oral irrigators have been applied in the art for purposes such as interdental cleaning (flossing). For this purpose, these devices, also known as interdental cleaners, have turned out to be greatly effective. Effective cleaning of the dental interproximal space would normally be at odds with delivering substances to said space. Rather, the interdental cleaning serves the purpose of removing substances (notably dental plaque) contained in the interproximal spaces. In accordance with the foregoing, WO 2013/093798 describes spray velocities running from 10 m/s to 300 m/s, e.g. 50 m/s. In the present invention, such generating devices are also used for the purpose of delivering substances to be retained in the interproximal space. This can be accomplished e.g. as described in WO 2016/050573.

The introduction of the particles comprising the oral care agent as a fluid jet, can be done by means of any device or unit capable of generating a fluid jet. E.g., in one embodiment, this can be a nozzle which is fed with the liquid under a pressure sufficient to generate the desired jet speed. In the method of the invention, the nozzle is directed to the mouth, such as to introduce the fluid jet into the oral cavity. Preferably, the device is adapted so as to enable directly reaching the interproximal spaces. To this end, the nozzle can take the form of a flexible or rigid tube, having a tip the dimensions of which allow a sufficient degree of precision at directing the fluid jet expelled therefrom to a desired location within the oral cavity, preferably such that localization directly into the interproximal spaces is possible. Alternatively, a syringe can be applied. An oral irrigator typically has a single nozzle, as the device is intended for the separate and precise cleaning of individual location, such as interproximal spaces, in the oral cavity.

In an interesting embodiment, a pulsed jet delivery of approximately 0.1 ml is provided by a plunger pump, for example driven by a pre-loaded spring. After each shot the syringe can be refilled from a larger suspension reservoir (as a container unit), while loading the spring.

The skilled person will be aware of devices and nozzles that are suitable for the aforementioned purposes. Particularly suitable types of devices are the above-mentioned oral irrigators, including interdental cleaners and liquid-assisted flossing devices.

An oral irrigator, such as an interdental cleaner, typically comprises a source of liquid; a system for moving a selected amount of liquid from the source thereof into a liquid pathway; a driving unit such as a pump or a source of pressurized gas, or a combination thereof; and a control arrangement for releasing a selected amount of gas into contact with the liquid, resulting in liquid being propelled out of a nozzle portion of the cleaner. Suitable devices are described, inter alia, in WO 2010/055433, WO 2010/055434, WO 2008/012707, WO 2014/068431.

The oral irrigators to which the invention applies, particularly function on the basis of a single nozzle being used at a time. These devices are adapted to be used for applying a liquid jet to each individual interproximal space separately. Also, it is to be understood that an oral irrigator is a device that, upon use, is held in the hand while kept for the most part outside of the mouth, or at least not in touch with the teeth. This is opposed to devices such as mouthpieces that are essentially to be placed over teeth, and kept in the mouth during their use. The fundamental distinction between such devices is known in the art, see e.g. the background section in US 2013/236851.

The fluid jet-generating devices suitable for use in the invention can be adapted to provide continuous jets, or separate shots of jets, or both. For the use and method of the present invention it is preferred if single shots can be provided. This would allow a greater precision in administering the above described particles to the various interproximal spaces one at a time. Such preferred devices are well-known in the art.

Preferably, the application device is provided with a container for retaining the particles prior to their delivery. E.g., the device can be provided with a reclosable aperture allowing a container to be attached as a separate module. Such a module is preferably replaceable so as to facilitate refilling the device with fresh particles. Also, such modules can then be exchanged so as to administer different particles having different oral care agents.

The fluid jet generator will be as discussed above in respect of oral irrigators, such as interdental cleaners. The container unit can be part of a fluid jet generating device, but it can also be a separate unit, whereby fluid communication is provided between an outlet of the container and an inlet of the jet generator. Such fluid communication can be provided by suitable tubes or flow lines, with suitable fixation of one to the other. Also, the jet generator unit can be provided with a holder for a cartridge, whereby the cartridge serves as a container for the liquid. The source of liquid, with which the container unit is in fluid communication, can be present in the container itself, viz. as a suspension comprising the particles. The source of liquid can also be provided from one container, and the particles from another. The source of liquid can also be an external source, to which the system of the invention can be hooked-up, or with which the system of the invention can be connected, so as to provide the required fluid communication between the container unit for the particles, and the source of liquid.

In a preferred embodiment, the fluid jet generator is used without a liquid, i.e., using an air only pulse for the delivery of the particles. Thus, dry particles preloaded with one or more oral care agents, can be delivered using currently existing oral irrigation technology involving air or gas pulses, such as AirFloss® device, yet without additional fluid as would be used in oral irrigation proper. To this end, in an interesting embodiment, an oral irrigation device can be provided with an alternative nozzle with attached particle cartridge. Reference is made to a specific design for general powder delivery using an AirFloss nozzle as disclosed in WO2016162782, which is highly suitable for carrying out the present invention as well.

In alternative embodiments, the application of the particles, so as to place them in between teeth, can be conducted by applying delivery forces other than fluidic and/or gas pulses. This can be a simple mechanical force, using a corresponding applicator, particularly a brush, a toothpick or a toothpick-like device, or an interdental brush. In an interesting embodiment a small cup is provided designed to hold the particles prior to delivery. In the event of brush, it is preferred for this to have bristles that are relatively short (e.g. 1-3 mm) and spaced relatively wide apart (such as 0.5-1.5 mm) so as to allow SAP particles in accordance with the invention to be held in between the bristles until being applied in between teeth.

The system of the invention preferably further comprises a dental appliance for cleaning teeth, selected from the group consisting of electric toothbrushes, electric flossing devices, and combinations thereof. Such dental appliances can be provided for various functions. This typically refers to a toothbrush, preferably an electrical toothbrush, more preferably a sonic power toothbrush having a vibrating brush head.

If not already provided by the jetting system of the invention itself, an electric flossing device, as is possibly comprised in the system of the invention, refers to such devices that serve to clean the interdental spaces generally by spraying air, by spraying liquid, or a combination thereof.

It is to be understood that the system can comprise its various parts as separate components, not packaged or provided together.

Particularly, the container holding the polymeric particles can well be provided as a separate entity, e.g., in the form of a bottle or tube holding the composition (comparable to a bottle of mouthwash or a toothpaste tube). The container can also be attached to the delivery device, particularly as a cartridge adapted for such an attachment, e.g. to an electric toothbrush (designed with a separate fluid delivery system), flossing device or an oral irrigator, such as a Philips Sonicare AirFloss or Philips Sonicare Toothbrush, with a delivery pump.

In an interesting further embodiment, the system according to the invention comprises a power module and one or more dental appliance heads that can be removably attached to said power module. This typically refers to having an electric toothbrush and/or an electric flossing device, both preferably provided as functional modules in the form of dental appliance heads.

While the invention has been illustrated and described in detail in the drawings and foregoing description, such illustration and description are to be considered illustrative or exemplary and not restrictive; the invention is not limited to the disclosed embodiments.

For example, it is possible to employ particles that have been preloaded with one oral care agent, and that, before delivery, are combined with an aqueous fluid comprising a further oral care agent. I.e., one or more agents can be contained in the particles, whilst one or more other agents are provided separately, e.g. as an aqueous solution.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain features of the invention are recited in mutually different dependent claims does not indicate that a combination of these features cannot be used to advantage. Any reference signs in the claims should not be construed as limiting the scope.

In summary, there is disclosed a system and method for the delivery, into an oral cavity and notably an interdental space, of oral care active agents contained in and/or on polymer particles. The particles are made of one or more superabsorbent polymers (SAP), and are of size generally small enough to be easily applied into an interdental space. To this end, the particles typically have a length of below 1.5 mm. By virtue of the SAP's ability of absorbing several times its own weight in water, the particles will swell once in contact with saliva. As a result, the volume of the particles as applied in between teeth increases by at least eight times, thereby effectively making the particles larger than the average interdental gap size. The particles, once swollen, are thus held more firmly between the walls of the interdental space, thus preventing them from being easily washed away.

The invention will be further explained hereinafter with reference to the examples and figures. These illustrate the invention, but do not limit it.

Example 1

Diapers contain absorbance material consisting of super absorbent polymers (SAP). Particles have been removed and collected from a diaper. It was tested how much water needed to be added to form a hydrogel. This occurred upon the addition of more than ten times the particles' volume, resulting in a hydrogel of visibly increased volume.

Particles as removed from the diaper were applied to a teeth model. (Typodont Frasaco AG3). The particles were applied using a manual toothbrush. Thereby care had to be taken to prevent the particles from sticking at the gum line, rather than being applied in between teeth.

In an improvement hereof, a small amount of water was added (i.e., well below the above-mentioned volume), resulting in pre-swelling into a jelly substance. This facilitated the application into interdental spaces by means of a toothbrush.

Additional water was added with a pipet which allowed the particles to swell (and for the pre-swollen particles: to further swell) and form a hydrogel. In the teeth model, the hydrogel filled the complete interdental space area. Excess gel, if any, will in practice be wiped away with the tongue but it can also be brushed away. By brushing the hydrogel is pushed through the interdental space and therefore comes out at the other side. This proves that the entire interdental space is filled with hydrogel.

It was attempted to remove the hydrogel from the interdental area. Even after rinsing under tap water, hydrogel was still present. Additional methods (toothpick, AirFloss) were necessary to remove the hydrogel. This proves that the swollen particles stick well in the interdental space.

Example 2

In this experiment the particles, obtained as in Example 1, have been soaked in a mouth rinse containing antimicrobial ingredients (BreathRx mouthwash (BRx)). After addition of the BRx to the beads, the beads were washed with phosphate buffered saline (PBS) for 1 h at 37° C. After washing the PBS was removed and human pooled saliva and plaque with artificial saliva medium was added, and a growth curve (FIG. 3, curve (a) Particels+BRx) was made of this culture to see if the washed antimicrobial hydrogel has an effect on the growth of the bacteria. As a control wells treated with the same amount of BRx without the beads and also washed with PBS were included (FIG. 3 curve (b) BRx), and wells not treated with any agents (FIG. 3 curve (c) Control). The results show that BRx without the particles had no substantively in the wells, as growth was similar to the control without any agents. However, in the presence of SAP particles that had taken up the BRx and were washed in PBS, the growth of the bacteria was delayed for over 10 h, showing that sufficient antimicrobial agents remained in the beads even after washing for a significant plaque reducing effect.

Figure 3:
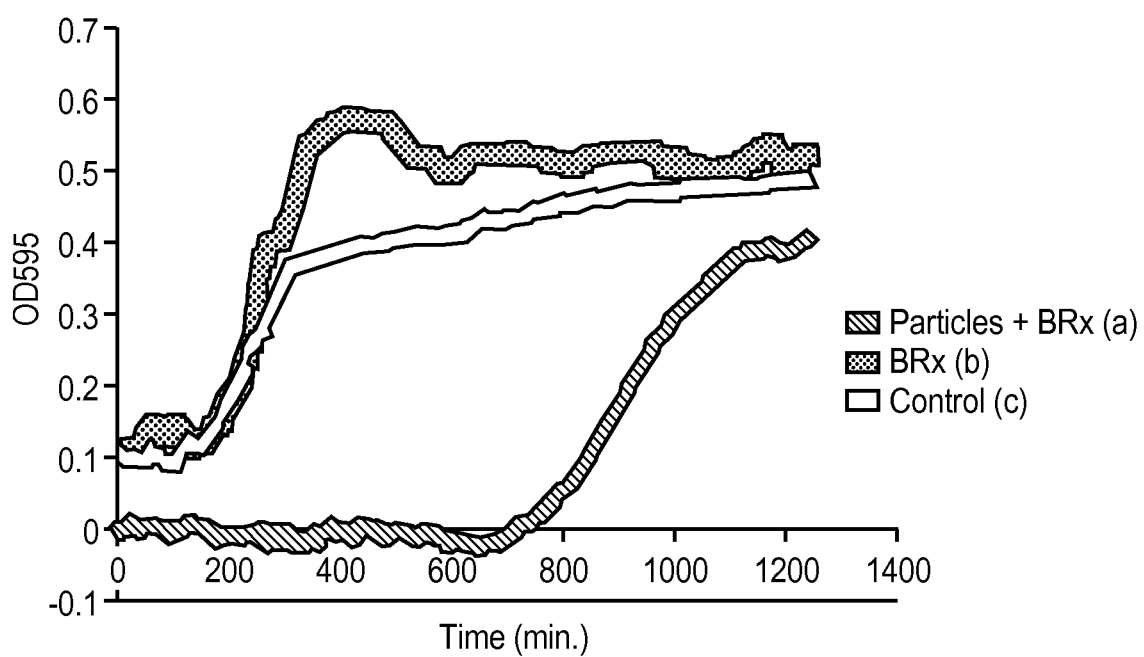
FIG. 3 is a graph representing results of inhibiting the growth of saliva biofilm using particles of the invention. It shows that growth of saliva biofilm is inhibited when particles soaked in BreathRx are present.

This is shown in FIG. 3, by plotting optical density at 595 nm (OD595), which is a conventional method to measure bacterial growth, on the y-axis, against time (in minutes, x-axis). Three curves are shown:
(a) Particles+active agent;
(b) Active agent;
(c) Control (without active agent).

The invention claimed is:

1. A system for the application of an oral care agent to an interdental space within an oral cavity of a subject, the system comprising:
(a) a first container holding one or more polymer particles each having an initial volume and at least one size dimension equal to or smaller than 1.5 millimeters, and having a shortest size dimension of at least 0.1 mm and a longest size dimension 1.5 to 3 times as long as the shortest size dimension prior to swelling, wherein the size dimensions are the length, width, height, body diagonal or diameter of the particle; wherein the particles comprise a super absorbent polymer selected from the group consisting of crosslinked polymers based on sodium polyacrylate; polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile;
(b) a second container holding the oral care agent; and
(c) an applicator for the interdental delivery of the one or more polymer particles comprising the oral care agent, wherein the one or more polymer particles swell to at least eight times the initial volume after being delivered to the interdental space.

2. A preparation comprising one or more polymer particles for the delivery of an oral care agent to an interdental space within an oral cavity of a subject, the one or more polymer particles having an initial volume and at least one size dimension equal to or smaller than 1.5 millimeters, and have having a shortest size dimension of at least 0.1 mm and a longest size dimension 1.5 to 3 times as long as the shortest size dimension prior to swelling, wherein the size dimensions are the length, width, height, body diagonal or diameter of the particle; wherein the one or more polymer particles comprise:

a super absorbent polymer selected from the group consisting of crosslinked polymers based on sodium polyacrylate; polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile; and the oral care agent;

wherein the one or more polymer particles swell to at least eight times the initial volume after being delivered to the interdental space.

3. The preparation according to claim 2, wherein the at least one size dimension equal to or smaller than 1.5 millimeters is the largest dimension of the one or more polymer particles.

4. The preparation according to claim 2, wherein the super absorbent polymer forms a hydrogel upon absorbing water.

5. The preparation according to claim 2, wherein the one or more polymer particles comprise a mucoadhesive coating comprising chitosan.

6. The preparation according to claim 2, wherein the oral care agent is selected from the group consisting of: anti-plaque agents, anti-tartar agents, anti-gingivitis agents, anti-caries agents, anti-bacterial agents, anti-periodontitis agents, mineralization agents, bleaching agents, and combinations thereof.

7. A method for administering an oral care agent to an interdental space within the oral cavity of a subject, the method comprising:

providing one or more polymer particles each having an initial volume and at least one size dimension equal to or smaller than 1.5 millimeters, and having a shortest size dimension of at least 0.1 mm and a longest size dimension 1.5 to 3 times as long as the shortest size dimension prior to swelling, wherein the size dimensions are the length, width, height, body diagonal or diameter of the particle, and each of the one or more polymer particles comprising:

a super absorbent polymer selected from the group consisting of crosslinked polymers based on sodium polyacrylate; polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile; and the oral care agent; and delivering the one or more polymer particles to the interdental space within the oral cavity, whereupon the one or more polymer particles are configured to swell to at least eight times the initial volume.

8. The method according to claim 7, wherein the at least one size dimension equal to or smaller than 1.5 millimeters is the largest dimension of the one or more polymer particles.

9. The method according to claim 7, wherein the one or more polymer particles are delivered to the interdental space with an applicator device for delivering the one or more polymer particles to the interdental space.

10. The method according to claim 7, wherein the one or more polymer particles comprise the oral care agent.

11. The method according to claim 9, wherein the oral care agent is added to the one or more polymer particles within the applicator device.

12. The method according to claim 7, wherein the method is for maintaining or improving oral health of the subject.

13. The method according to claim 9, wherein the applicator device is selected from the group consisting of oral irrigators, electrical toothbrushes, and combinations thereof.

* * * * *